United States Patent [19]
Löfås

[11] Patent Number: 6,143,513
[45] Date of Patent: Nov. 7, 2000

[54] METHOD AND KIT FOR DETECTING BETALACTAM-CONTAINING COMPOUNDS

[75] Inventor: Stefan Löfås, Uppsala, Sweden

[73] Assignee: Biacore AB, Uppsala, Sweden

[21] Appl. No.: 09/338,934

[22] Filed: Jun. 23, 1999

[51] Int. Cl.[7] .............................. C12Q 1/37; C12Q 1/00; G01N 33/53
[52] U.S. Cl. .............................. 435/24; 435/23; 435/7.1; 435/4
[58] Field of Search ................................ 435/24, 23, 7.1, 435/4

[56] References Cited

U.S. PATENT DOCUMENTS

| | | | |
|---|---|---|---|
| 4,546,076 | 10/1985 | Degelaen et al. | 435/24 |
| 4,686,182 | 8/1987 | Drake | 435/24 |

FOREIGN PATENT DOCUMENTS

| | | |
|---|---|---|
| 48711/85 | 4/1986 | Australia . |
| 76226/91 | 11/1991 | Australia . |
| 085 667 A2 | 8/1983 | European Pat. Off. . |

OTHER PUBLICATIONS

Frere et al., "Enzymatic Method for Rapid and Sensitive Determination of β–Lactam Antibiotics," *Antimicrobial Agents And Chemotherapy* 18(4):506–510, 1980.

*Primary Examiner*—Louise N. Leary
*Attorney, Agent, or Firm*—Seed Intellectual Property Law Group LLC

[57] ABSTRACT

Methods and kits are disclosed for detecting betalactam-containing compounds in a sample, and typically liquid products intended for human consumption such as milk. Betalactam-containing compounds include the class of beta-lactam antibiotics which may be present as undesired contaminates of milk. The methods involves contacting the sample with a D,D-carboxypeptidase and a substrate having a carboxyterminal D-alanine-D-alanine to form a reaction mixture, wherein the D,D-carboxypeptidase is capable of cleaving the terminal D-alanine from the substrate to yield a cleaved substrate. In an optional step, the reaction mixture is further contacted with a ligand specific to the cleaved substrate or substrate. The cleaved substrate or substrate of the reaction mixture, or the ligand specific to the cleaved substrate or substrate, is then captured by a surface-bound binding partner, with the amount of captured material being indicative to the amount of betalactam-containing compound in the sample. Kits for performing the methods of this invention are also disclosed.

30 Claims, No Drawings

METHOD AND KIT FOR DETECTING BETALACTAM-CONTAINING COMPOUNDS

TECHNICAL FIELD

This invention relates generally to enzymatic methods and kits for detecting betalactam-containing compounds and, more specifically, to the use of a biosensor to detect the presence of a betalactam antibiotic in a liquid sample and kits for use therewith.

BACKGROUND OF THE INVENTION

Antibiotic contamination of milk and related dairy products is a significant problem in the dairy industry. A major source of such contamination are betalactam antibiotics (e.g., penicillins and cephalosporins), which have been administered to cows to treat mastitis or other infections. More generally, large quantities of milk and related dairy products are discarded each year due to betalactam antibiotic contamination, thereby causing substantial economic losses.

There are several known procedures for detecting betalactam antibiotics in a liquid sample, known procedures such as microbiological and chemical techniques, high-performance liquid chromatography, and enzyme immunoassays. For example, microbiological (agar diffusion) techniques permit detection of about 0.1 to 0.5 microgram of antibiotic per milliliter of sample (i.e., µg/ml), but such techniques are rather time-consuming (see, e.g., Bennett et al., "Simplified Accurate Method For Antibiotic Assay of Clinical Specimens," *Appl. Microbiol.* 14:170–177, 1966; Cole et al., "Metabolism of Penicillins to Penicilloic Acids and 6-APA in Man and its Significance in Assessing Penicillin Absorption," *Antimicrob. Agents Chemother.* 3:463–468, 1973; and Spyker et al., "Pharmacokinetics of Amoxicillin: Dose Dependence After Intravenous, Oral and Intramuscular Administration," *Antimicrob. Agents Chemother.* 11:132–141, 1977). Chemical procedures are generally somewhat faster, but are typically much less sensitive (see, e.g., Marelli, L. P., "Analytical Procedures For Cephalosporins" in E. H. Flynn (ed.), *Cephalosporins and Penicillins*, Academic Press, Inc., New York, 1972, pp. 609–635). High-performance liquid chromatography has been used to estimate amoxycillin and ampicillin in sera and urines (see, e.g., Vrée et al., "Rapid Determination of Amoxycillin (clamoxyl) and Ampicillin (penbritin) in Body Fluids of Many By Means of High Performance Liquid Chromatography," *J. Chromatogr.* 145:496–501, 1978) and cephalosporin C in fermentation media (see, e.g., Alemanni et al., "HPLC Routine Analysis of Biosynthetic Active Compounds in Fermentation Media," *Chromatographia* 12:396–398, 1979); in these chromatographic techniques, however, minimal concentrations of about 0.5 µg/ml are generally necessary. Finally, an enzyme immunoassay has been devised which detects ampicillin at concentrations as low as 10 ng/ml; betalactam antibiotics other than ampicillin, however, have not been investigated by this technique (see, e.g., Kitagawa et al., "Novel Enzyme Immunoassay of Three Antibiotics: New Methods For Preparation of Antisera to the Antibiotics and for Enzyme Labeling Using a Combination of Two Hetero-Bisfunctional Reagents," S. B. Pai (ed.), *Enzyme Labelled Immunoassay of Hormones and Drugs*, Walter de Gruyter, Inc., Hawthorne, N.Y., 1978, pp. 59–66).

In addition to these known procedures, several commercial methods have been developed for detecting betalactam antibiotics in milk. For example, U.S. Pat. Nos. 4,239,745 and 4,239,852 to Charm describe commercial methods for detecting an antibiotic in a liquid sample (e.g., milk) based on the competitive binding between the antibiotic contaminant and a tagged antibiotic to receptor sites on bacterial cells. These commercial assays, like some of the other proposed assays, are based on immunochemical reactions and utilize antibodies directed against specific betalactam antibiotics. There are, however, several disadvantages associated with these types of assays, including: (1) the sample generally requires removal of interfering materials; and (2) the sample additives generally require a mixture of antibodies with specificities and high affinities for different betalactam antibiotics.

Of the commercial methods developed for detecting the presence of betalactam antibiotics, the enzymatic methods based on the ability of betalactam antibiotics to inactivate a specific D,D-carboxypeptidase bacterium Actinomadura-R39 are of particular interest (see, e.g., Frère et al., "Enzymatic Method for Rapid and Sensitive Determination of β-Lactam Antibiotics," *Antimicrobial Agents and Chemotherapy*, p. 506–510, 1980). Although other bacterial D,D-carboxypeptidase are known to be reversibly inhibited by betalactam antibiotics, the R39 enzyme has been preferentially used because the rate of inactivation is very rapid and the reversal of inhibition is very slow. Thus, over short periods of time, exposure of R39 enzyme to a betalactam antibiotic results in a stoichiometric loss of R39 catalytic activity. Accordingly, measurement of remaining R39 activity after exposure to test samples (suspected of containing a betalactam antibiotic) provides an assay for detecting the antibiotic.

More specifically, the assay as described by Frère et al. is similar to a commercial test known as PENZYM™ sold by UCB Bioproducts (Brussels, Belgium). This commercial test, however, is rather time-consuming and involves a number of steps and separate reagents. The first step involves an incubation (e.g., five minutes) of the test sample with the carboxypeptidase. If the test sample contains a betalactam antibiotic, a certain amount of the enzyme will be inactivated during the incubation depending on the amount of antibiotic present. The next two steps involve adding a substrate for the carboxypeptidase, which is a peptide containing a carboxyterminal D-alanine-D-alanine. This is followed by another incubation (e.g., 15 minutes) during which the terminal D-alanine is cleaved from the substrate. Other reagents are added during this incubation period to measure the amount of cleaved D-alanine. The liberated D-alanine is oxidized into pyruvic acid by a D-amino acid oxidase enzyme with simultaneous formation of hydrogen peroxide. The hydrogen peroxide oxidizes an organic redox indicator (e.g., o-dianisidine), which provides a colorimetric read-out. Sulfuric acid is added at the end of the incubation period to terminate the reaction and stabilize the color formation.

The PENZYM™ kit is supplied with seven separate reagents including: (1) the D,D-carboxypeptidase; (2) buffer for the D,D-carboxypeptidase; (3) substrate for the D,D-carboxypeptidase (($Acetyl)_2$-L-Lys-D-ala-D-ala); (4) flavin adenine dinucleotide, cofactor of the D-amino acid oxidase; (5) peroxidase; (6) o-dianisidine and (7) D-amino acid oxidase. The use of this kit, however, suffers from a number of disadvantages. First, the sequential addition of reagents in several different steps is required. Second, the amount of time required to complete the assay (i.e., about 20 to 30 minutes) is considered excessive, particularly by milk haulers. Finally, an excessive number of separately-packaged reagents must be handled.

Accordingly, there is a need in the art for improved methods for detecting betalactam-containing compounds, particularly in the context of detecting the presence of a betalactam antibiotic in a liquid sample. The present invention fulfills these needs, and provides further related advantages.

SUMMARY OF THE INVENTION

In brief, the present invention is generally directed to detection of betalactam-containing compounds and, more specifically, to methods and kits for detecting a betalactam antibiotic in a sample. In one embodiment of this invention, methods are disclosed for detecting a betalactam-containing compound in a sample by contacting the sample with a D,D-carboxypeptidase and a substrate having a carboxyterminal D-alanine-D-alanine to form a reaction mixture, wherein the D,D-carboxypeptidase is capable of cleaving the terminal D-alanine from the substrate to yield a cleaved substrate.

In an optional step, the reaction mixture is further contacted with a ligand specific to the cleaved substrate or a ligand specific to the substrate to form a modified reaction mixture, wherein the ligand specific to the cleaved substrate is capable of binding to the cleaved substrate to form a ligand/cleaved substrate complex, and wherein the ligand specific to the substrate is capable of binding to the substrate to form a ligand/substrate complex. This optional step may occur in a step subsequent to formation of the reaction mixture or, in the embodiment wherein a ligand specific to the cleaved substrate is employed, simultaneously with formation of the reaction mixture.

The methods then involve capturing on a sensing surface (i) the cleaved substrate or the substrate of the reaction mixture, or (ii) the ligand/cleaved substrate complex or the ligand/substrate complex of the modified reaction mixture, or (iii) the ligand specific to the cleaved substrate or the ligand specific to the substrate of the modified reaction mixture, by a surface-bound binding partner to (i) or (ii) or (iii).

In more specific embodiments, the sample containing the betalactam-containing compound is a liquid sample, such as a liquid food product. However, the sample may also be a solid form that is either extract by or suspended within a liquid sample. In a preferred embodiment, the liquid sample is milk and the betalactam-containing compound to be detected is a betalactam antibiotic, such as a penicillin or cephalosporin.

The D,D-carboxypeptidase is typically obtained from Actinomandura strain R39 or Streptomyces strain R61, and the substrate is a peptide having AA-D-alanine-D-alanine at the carboxy end of the peptide, wherein AA represent one or more amino acids, or modified amino acids, such as N,N-diacetyl-L-lysyl-D-alanine-D-alanine or N-acetyl-L-lysyl-D-alanine-D-alanine. In the optional step to form the modified reaction mixture, the ligand specific to the cleaved substrate or a ligand specific to the substrate is an antibody.

On the sensing surface, the choice of the surface-bound binding partner depends upon the nature of the target to be bound thereby. For example, when the cleaved substrate or the substrate of the reaction mixture is to be captured, the surface-bound binding partner is typically a surface-bound antibody specific to the cleaved substrate or the substrate. Similarly, when the ligand/cleaved substrate complex or the ligand/substrate complex of the modified reaction mixture is to be detected, the surface-bound binding partner is typically a surface-bound antibody specific to the ligand/cleaved substrate complex or the ligand/substrate complex. In contrast, when the ligand specific to the cleaved substrate or the ligand specific to the substrate of the modified reaction mixture is to be captured (e.g., an antibody), the surface-bound binding partner is typically a surface-bound cleaved substrate or surface-bound substrate, respectively.

In a preferred embodiment of this invention, the sensing surface is a surface of an affinity biosensor, and more preferably a sensing surface of a biosensor that utilizes surface plasmon resonance, such as the "BIACORE instrument" as discussed in greater detail below.

In another embodiment, the method further comprises the step of terminating the reaction between the D,D-carboxypeptidase and the substrate in the reaction mixture or modified reaction mixture. Termination may be employed prior to the step of capturing to provide consistency from measurement to measurement, particularly when varying lengths of time may occur between the steps of contacting and capturing.

In still a further embodiment of this invention, kits are disclosed for detecting a betalactam-containing compound in a sample. A representative kit of this invention contains (1) a substrate having a carboxyterminal D-alanine-D-alanine, (2) a D,D-carboxypeptidase capable of cleaving the terminal D-alanine from the substrate to yield a cleaved substrate, (3) a ligand specific to the cleaved substrate, and (4) a binding partner of (3) above, wherein the binding partner is capable of being bound to a sensing surface of a biosensor. In preferred embodiments, the ligand specific to the cleaved substrate is an antibody, and the binding partner is a surface-bound cleaved substrate. In the context of the BIACORE instrument, the kit preferably includes a sensor surface having surface-bound cleaved substrate. The kits of this invention may also contain suitable buffers and/or carriers for the above components, as well as for the reaction and modified reaction mixtures.

These and other aspects of this invention will be evident upon reference to the attached figure and following detailed description.

DETAILED DESCRIPTION OF THE INVENTION

As mentioned above, the present invention is directed to methods and kits for detecting betalactam-containing compounds. The phrase "betalactam-containing compounds" represents a class of compounds that contain at least one betalactam moiety as represented by structure (I) below. Thus, in the practice of this invention, any compound containing at least one betalactam moiety constitutes a betalactam-containing compound. In a more specific embodiment, the betalactam-containing compound is an antibiotic, such as penicillins or cephalosporins. For example, penicillins contain a betalactam moiety as represented by structure (II), wherein A represents various moieties depending upon the specific nature of the penicillin (e.g., Penicillin G, N, O, S, V, etc.), while structure (III) represents cephalosporins wherein B/B' represents various moieties depending upon the specific nature of the cephalosporin or similar compound (e.g., Cephalosporin C, Cephalothin, Cephamycin, Cephaparin, Cephradine, etc.).

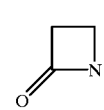

(I)

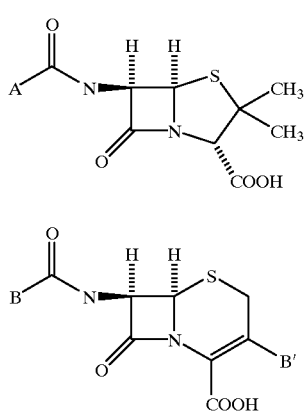

Betalactam-containing compounds of this invention inhibit the activity of D,D-carboxypeptidases on substrates cleavable thereby, specifically substrates having a D-carboxyterminal alanine. In other words, when a sample containing a betalactam-containing compound is contacted with a D,D-carboxypeptidase and substrate, the amount of substrate that is cleaved by the D,D-carboxypeptidase to the cleaved substrate form will depend upon the amount of the betalactam-containing compound in the sample. While betalactam-containing antibiotics are known to reversibly inhibit a number of D,D-carboxypeptidases, in the practice of this invention the D,D-carboxypeptidase is preferably one wherein the rate of inactivation is very rapid, while the rate of reversal of inhibition is very low. To this end, preferred D,D-carboxypeptidases included (but are not limited to) the D,D-carboxypeptidase isolated from the bacterium strain Antinomadura-R39 (UCB Bioproducts, Brussels, Belgium) (hereinafter referred to as the "R39 enzyme"), and the D,D-carboxypeptidase isolated from the bacterium strain Streptomyces R61 (Frère et al., *Methods Enzymol,* 45B:610–636, 1976) (hereinafter referred to as the "R61 enzyme").

In the practice of this invention, the amount of betalactam-containing compound in a sample is detected by contacting the sample with a D,D-carboxypeptidase and a substrate having a carboxyterminal D-alanine-D-alanine. The sample itself may be a liquid sample, such as a liquid food product, or a solid sample that is solubilized or otherwise extracted to yield a liquid sample. While the present invention has utility over a wide range applications, in a preferred embodiment the sample is a liquid sample intended for human consumption, such as milk and related milk products like, for example, cheese and yogurt. For example, in the case of milk, betalactam antibiotics are often administered to dairy cows for treating mastitis. Such antibiotics, however, are considered contaminates in milk and related dairy products, and must fall to an acceptably low value before it can be sold to humans. Thus, a method of detecting the presence (or absence) of a betalactam antibiotic in milk, for example, is of important commercial value.

Prior techniques of detecting betalactam antibiotics in milk, such as those disclosed by Frère et al. as discussed in the Background section, employ a D,D-carboxypeptidase and substrate, but detect formation of the cleaved D-alanine through a series of time-consuming and multiple step procedure involving a number of reagents. The present invention avoids these shortcomings by detecting the cleaved substrate (or substrate). In this context, the "cleaved substrate" is that portion of the substrate remaining after cleavage of the carboxyterminal D-alanine. Alternatively, and in a more preferred embodiment, the cleaved substrate (or substrate) is contacted with a ligand specific to the cleaved substrate (or substrate) to form a ligand/cleaved substrate complex (or ligand/substrate complex). Any remaining ligand not complexed with cleaved substrate (or substrate) is then detected. Since the ligand, which is typically an antibody, has a greater mass than the cleaved substrate (or substrate), detection of the ligand by a mass-sensitive technique yields greater sensitivity to the detection method. Alternatively, the ligand/cleaved substrate complex (or ligand/substrate complex) may also be detected.

More specifically, the methods of this invention are directed to detecting a betalactam-containing compound within a sample by contacting the sample with a D,D-carboxypeptidase and a substrate having a carboxyterminal D-alanine-D-alanine to form a reaction mixture. As mentioned above, preferred D,D-carboxypeptidases of this invention include the R39 enzyme and the R61 enzyme, while preferred substrates are peptides or modified peptides having the structure AA-D-alanine-D-alanine at the carboxy terminal, wherein AA represent one or more amino acids, or modified amino acids, such as N,N-diacetyl-L-lysyl-D-alanine-D-alanine or N-acetyl-L-lysyl-D-alanine-D-alanine.

The sample potentially containing the betalactam may be of either a liquid or solid form. In the case of solids, the sample is first solubilized, dissolved, extracted, suspended or otherwise made into a liquid from. The liquid sample is then contacted with the D,D-carboxypeptidase and substrate, typically by addition of specific amounts of each into a known volume of sample. The amount of D,D-carboxypeptidase and substrate added to a given volume of sample normally ranges from 10 to 50 pmol D,D-carboxypeptidase and from 50 to 1,000 nmol substrate to 0.5 to 2.0 ml of sample. The ratio for substrate to carboxypeptidase is preferably chosen to be in the range from 1,000–50,000 (i.e., a clear excess of substrate due to the enzymatic turnover by the peptidase). The reaction solution is preferably incubated for 2–15 minutes at 35° C.–45° C.

When the D,D-carboxypeptidase is added to a sample containing no betalactam-containing compound, the D,D-carboxypeptidase cleaves the substrate unhindered by the inhibitory effect of the betalactam-containing compound. Unless stopped prior to complete reaction, all of the substrate in the sample will be cleaved by the D,D-carboxypeptidase to generate cleaved substrate. In contrast, to the extent that the sample contains a betalactam-containing compound, the betalactam-containing compound will inhibit the D,D-carboxypeptidase, thereby slowing the rate of formation (and resulting concentration) of the cleaved substrate in the reaction mixture. By detecting the amount of cleaved substrate in the reaction mixture (or amount of substrate remaining in the reaction mixture), the amount of betalactam-containing compound in the sample may be determined.

Alternatively, and in a more preferred embodiment, the cleaved substrate is contacted with a ligand specific to the cleaved substrate to form a ligand/cleaved substrate complex. In this context, the "ligand" is any binding partner to the cleaved substrate, and typically an antibody specific to the cleaved substrate, and the "complex" is the resulting interaction pair. The ligand specific to the cleaved substrate can be added to the sample simultaneously with the D,D-carboxypeptidase and substrate (in which case the modified reaction mixture is formed simultaneously with the reaction mixture), or can be added subsequently to formation of the reaction mixture.

In a further alternative embodiment, the substrate is contacted with a ligand specific to the substrate to form a ligand/substrate complex. However, in this embodiment the ligand specific to the substrate is preferably added subsequent to formation of the reaction mixture to avoid interfering with the action of the D,D-carboxypeptidase on the substrate.

Following formation of the reaction mixture by contacting the D,D-carboxypeptidase with the substrate, and optionally following formation of the modified reaction mixture by contact with the ligand specific to the cleaved substrate (or substrate), detection of the desired target may be accomplished by use of an appropriate surface-bound binding partner. When detection of the cleaved substrate (or substrate) of the reaction mixture is desired, the surface-bound binding partner is a ligand specific to the cleaved substrate (or substrate), typically a surface-bound antibody to the cleaved substrate (or substrate).

On the other hand, when a modified reaction mixture is formed, either the ligand itself or the ligand/cleaved substrate complex (or ligand/substrate complex) may be detected. In the embodiment where the ligand specific to the cleaved substrate (or substrate) is to be detected, the surface-bound binding partner is an analyte to which the ligand binds to form a binding pair. Typically, the surface-bound binding partner is cleaved substrate which, upon contact with the ligand, forms a surface-bound cleaved substrate/ligand binding pair. In the embodiment where the ligand/cleaved substrate complex (or ligand/substrate complex) is to be detected, the surface-bound binding partner is a ligand that specifically recognizes the formed ligand/substrate complex, to which the complex binds to form a binding pair. Typically, the surface-binding partner is an antibody which, upon contact with the complex, forms a surface-bound antibody/complex binding pair.

The surface-bound binding partner may be bound to a sensing surface by any of a variety of known techniques, such as by, for example, known ligand immobilization techniques via native —NH$_2$, —SH, —CHO, and —COOH groups. Such techniques are well known in the art, and suitable reagents and procedures for achieving the desired binding partner immobilization are readily available. Accordingly, a sensing surface in accordance with the present invention may comprise a solid metal support (e.g., gold or silver) having a coating of a densely packed organic monolayer thereon (as is disclosed in U.S. Pat. No. 5,436.161, which is incorporated herein by reference in its entirety.) The sensing surface may further comprise a biocompatible porous matrix like, for example, a hydrogel (e.g., a polysaccharide such as dextran) coupled to the organic monolayer coating. Such a hydrogel may then be appropriately derivatized to contain hydroxyl, carboxyl, amino, aldehyde, carbonyl, epoxy, or vinyl groups for immobilization of the binding partner to yield a surface-bound binding partner.

In a typical embodiment of this invention, the sensing surface is a surface of a biosensor (having the desired binding partner immobilized thereon), and the detection techniques involves contacting the immobilized binding partner with the reaction mixture or modified reaction mixture. Typically, such detection techniques include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging, such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers. While certain aspects of the present invention are hereinafter illustrated in the context of the BIACORE instrument (BIACORE AB, Uppsala, Sweden) with its SPR-based technology, it is to be understood that the present invention is not limited to such systems.

More specifically, it is to be understood that the term "biosensor," as used within the context of the present invention, is to be construed broadly so as to encompass any analytical device capable of detecting biomolecular interactions between the target of interest in the reaction mixture or modified reaction mixture and the surface-bound binding partner of the biosensor, provided that the device includes at least one sensing element coupled to a transducer. Accordingly, the term biosensor includes not only analytical devices that use flow systems to contact sample with one or more sensing surfaces (like the microfluidic structures of the BIACORE instrument as discussed below), but also covers analytical devices that use non-flow systems to contact sample with one or more sensing surfaces like the cuvette structure employed by some biosensor instrumentation. As such, the present invention is applicable to both types of flow and non-flow systems.

In this regard, a representative class of biosensor instrumentation is sold by BIACORE AB (Uppsala, Sweden) under the trade name BIACORE® (referred to as "the BIACORE instrument"). The BIACORE instrument includes a light emitting diode, a sensor chip covered with a thin gold film, an integrated fluid cartridge and photo detector. Incoming light from the diode is reflected in the gold film and detected by the photo detector. At a certain angle of incidence ("the SPR angle"), a surface plasmon wave is set up in the gold layer, which is detected as an intensity loss or "dip" in the reflected light. (Note that a more complete description of this representative BIACORE instrument including its microfluidic block unit for flowing solutions therein may be found in U.S. Pat. No. 5,313,264, which is incorporated herein by reference in its entirety.)

The SPR angle depends on the refractive index of the medium close to the gold layer. In the BIACORE instrument, dextran is typically coupled to the gold surface, and a ligand is bound to the dextran layer. The analyte of interest is injected in solution form onto the sensor surface through a fluid cartridge. Since the refractive index in the proximity of the gold film depends upon (1) the refractive index of the solution (which is constant) and, (2) the amount of material bound to the surface, the interaction between the bound ligand and analyte can be monitored as a function of the change in SPR angle.

A typical output from the BIACORE instrument is a "sensorgram," which is a plot of response (measured in "resonance units" or "RU") as a function of time. An increase of 1000 RU corresponds to an increase of mass on the sensor surface of approximately 1 ng/mm². As sample containing an analyte contacts the sensor surface, the ligand bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicted on the sensorgram by a drop in RU over time as analyte dissociates from the surface-bound ligand.

Accordingly, and in one embodiment of the present invention, detection of cleaved substrate (or substrate) of the reaction mixture may be accomplished by use the BIA-CORE instrument having an appropriate ligand specific to the cleaved substrate (or substrate) immobilized on the sensing surface. Alternatively, detection of the ligand specific to the cleaved substrate (or substrate) may be accomplished by use of the BIACORE instrument having an appropriate binding partner, such as cleaved substrate (or substrate) immobilized on the sensing surface. In still a further embodiment, detection of the ligand/cleaved substrate complex (or ligand/substrate complex) may be accomplished by use of the BIACORE instrument having an appropriate binding partner, such as an antibody immobilized on the sensing surface. A quantitative determination is preferentially done by producing a calibration curve with standard samples with known quantities of betalactam.

In a further embodiment, the method of this invention further comprises a step of terminating the reaction between the D,D-carboxypeptidase and the substrate in the reaction mixture or modified reaction mixture. This termination step may be accomplished by addition of an excess of betalactam, thereby inhibiting the activity of the D,D-carboxypeptidase. Alternatively, a substance or conditions known to destroy the enzymatic activity of the D,D-carboxypeptidase may be added or applied to the reaction mixture or modified reaction mixture. Representative examples include (but are not limited to) addition of strong acid or base, denaturating detergent, organic solvents or cooling on ice bath, which will significantly slow down or stop the enzymatic reaction. The termination step is typically employed in order to perform the assay under conditions when multiple samples are assayed at various times.

In another embodiment of this invention kits are disclosed for performing the above methods. Such kits include at least the following components: (1) a D,D-carboxypeptidase, (2) a substrate having carboxyterminal D-alanine-D-alanine, and (3) a binding partner of the desired target to be captured on the sensing surface. In the embodiment wherein the cleaved substrate (or substrate) of the reaction mixture is to be captured, the binding partner is a binding partner of the cleaved substrate (or substrate). Alternatively, in the embodiment wherein the ligand specific to the cleaved substrate (or substrate) of the modified reaction mixture is to be captured, the binding partner is a binding partner of the ligand specific to the cleaved substrate (or substrate). In the embodiment, wherein the ligand/cleaved substrate complex (or ligand/substrate complex) is to be captured, the binding partner is a binding partner to the ligand/cleaved substrate complex (or ligand/substrate complex).

In addition to the above components, the kit may further include suitable buffers and/or carriers for the above components, as well as for the reaction and modified reaction mixtures.

In a preferred embodiment, the kit includes: (1) a substrate having a carboxyterminal D-alanine-D-alanine, (2) a D,D-carboxypeptidase capable of cleaving the terminal D-alanine from the substrate to yield a cleaved substrate, (3) a ligand specific to the cleaved substrate, and (4) a binding partner of (3) above, wherein the binding partner is capable of being bound to a sensing surface of a biosensor. Preferably the binding partner is cleaved substrate, and more preferably is immobilized on an appropriate sensor surface. For example, in the context of the BIACORE instrument, the kit preferably includes a sensor chip having cleaved substrate immobilized thereon. Suitable sensing chips in this context are based on the CM5 chip available from BIA-CORE which has immobilized thereon the cleaved substrate or a derivative thereof that is capable of binding the ligand specific to the cleaved substrate. Alternatively, the kit includes the CM5 chip, coupling reagents for immobilization of the cleaved substrate (or a derivative thereof), and the cleaved substrate (or a derivative thereof) suitable for immobilization on the CM5 chip.

The following example is provided by way of illustration, no limitation.

EXAMPLES

Example 1

Detection of Penicillin Within Milk

This example illustrates a representative method in accordance with the present invention for detecting the presence and amount of penicillin within a raw milk sample.

Raw milk sample (90 microliters) containing the suspected betalactam is mixed with 90 microliters of 100 mM HEPES buffer (pH 7.5) containing 200 mM NaCl, 6 mM $MgCl_2$ and 150 nmol $Ac_2$-L-Lys-D-Ala-D-Ala. To the reaction mixture is added 5.0 pmol R39 enzyme (in 20 microliters of 100 mM HEPES buffer (pH 7.5) containing 200 mM NaCl and 6 mM $MgCl_2$). The reaction mixture was incubated for 5 minutes at 40° C. The mixture is then rapidly cooled in an ice bath and placed in a BIACORE 2000 instrument for analysis. The BIACORE instrument is equipped with a CM5 sensor chip to which L-Lys-D-Ala-D-Ala has been immobilized using a standard amine coupling procedure which employs an EDC/NHS activation step. Using the autosampler unit in BIACORE 2000, 100 microliters of the reaction solution is mixed with 100 microliters of an antibody solution (1 pmol in 50 mM HEPES buffer containing 100 mM NaCl) and injected over the sensor chip. The antibody employed is selected to be specific for the part of the substrate containing the structure L-Lys-D-Ala-D-Ala. A response is recorded by the BIA-CORE instrument for a contact time of 2 minutes. The response level is compared with a calibration curve obtained in a similar fashion from samples having known amounts of betalactam, from which the betalactam content in the milk is determined.

While the methods and kits of the present invention have been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing description, and all changes that come within the meaning and range of equivalency of the claims are to be embraced within their scope.

I claim:

1. A method for detecting a betalactam-containing compound in a sample, comprising:

contacting the sample with a D,D-carboxypeptidase and a substrate having a carboxyterminal D-alanine-D-alanine to form a reaction mixture, wherein the D,D-carboxypeptidase is capable of cleaving the terminal D-alanine from the substrate to yield a cleaved substrate;

optionally contacting the reaction mixture with a ligand specific to the cleaved substrate or a ligand specific to the substrate to form a modified reaction mixture, wherein the ligand specific to the cleaved substrate is capable of binding to the cleaved substrate to form a ligand/cleaved substrate complex, and wherein the ligand specific to the substrate is capable of binding to the substrate to form a ligand/substrate complex; and capturing on a sensing surface (i) the cleaved substrate or the substrate of the reaction mixture, or (ii) the ligand/cleaved substrate complex or the ligand/substrate complex of the modified reaction mixture, or (iii) the ligand specific to the cleaved substrate or the ligand specific to the substrate of the modified reaction mixture, by a surface-bound binding partner thereto.

2. The method of claim 1 wherein the sample is a liquid sample.

3. The method of claim 1 wherein the betalactam-containing compound is a betalactam antibiotic.

4. The method of claim 3 wherein the betalactam antibiotic is penicillin or cephalosporin.

5. The method of claim 4 wherein the betalactam antibiotic is penicillin G, ampicillin, amoxicillin, cloxacillin, ceftifur, cephapirin, dicloxacillin or oxacillin.

6. The method of claim 1 wherein the sample is a liquid food product.

7. The method of claim 6 wherein the liquid food product is milk or a milk-related product.

8. The method of claim 1 wherein the sample is a solid food product solubilized in liquid carrier.

9. The method of claim 1 wherein the D,D-carboxypeptidase is obtained from Actinomandura strain R39 or Streptomyces strain R61.

10. The method of claim 1 wherein the substrate is a peptide having $AA_1$–$AA_2$-D-alanine-D-alanine at the carboxy end of the peptide, wherein $AA_1$ and $AA_2$ represent the same or different amino acids.

11. The method of claim 1 wherein the sample is a liquid sample and the D,D-carboxypeptidase and the substrate are added directly to the sample to form the reaction mixture.

12. The method of claim 1 wherein the modified reaction mixture is formed simultaneously with the reaction mixture by simultaneously contacting the sample with the D,D-carboxypeptidase, the substrate and the ligand specific to the cleaved substrate.

13. The method of claim 1 wherein the modified reaction mixture is formed subsequent to formation of the reaction mixture by contacting the sample with the D,D-carboxypeptidase and substrate, and subsequently contacting the reaction mixture with the ligand specific for the cleaved substrate or ligand specific for the substrate to form the modified reaction mixture.

14. The method of claim 1 wherein ligand specific to the cleaved substrate is an antibody.

15. The method of claim 1 wherein the ligand specific to the substrate is an antibody.

16. The method of claim 1 wherein the surface-bound binding partner for capturing the cleaved substrate or the substrate is a surface-bound antibody.

17. The method of claim 1 wherein the surface-bound binding partner for capturing the ligand/cleaved substrate complex or the ligand/substrate complex is a surface bound antibody.

18. The method of claim 1 wherein the surface-bound binding partner for capturing the ligand specific to the cleaved substrate is surface-bound cleaved substrate.

19. The method of claim 1 wherein the surface-bound binding partner for capturing the ligand specific to the substrate is surface-bound substrate.

20. The method of claim 1 wherein the sensing surface is a surface of a biosensor.

21. The method of claim 20 wherein the biosensor is an affinity biosensor that utilizes surface plasmon resonance.

22. The method of claim 1 further comprising the step of terminating the reaction between the D,D-carboxypeptidase and the substrate in the reaction mixture or the modified reaction mixture by adding an excess of a betalactam or by significantly changing the reaction conditions.

23. A kit for detecting a betalactam-containing compound in a sample, comprising:

a substrate having a carboxyterminal D-alanine-D-alanine;

a D,D-carboxypeptidase capable of cleaving the terminal D-alanine from the substrate to yield a cleaved substrate; and a binding partner of the substrate or the cleaved substrate, wherein the binding partner is capable of being bound on a sensing surface.

24. The kit of claim 23 wherein the binding partner is a binding partner of the cleaved substrate.

25. The kit of claim 24 wherein the binding partner is an antibody to the cleaved substrate.

26. The kit of claim 23 wherein the binding partner is a binding partner of the substrate.

27. The kit of claim 24 wherein the binding partner is an antibody to the substrate.

28. A kit for detecting a betalactam-containing compound in a sample, comprising:

a substrate having a carboxyterminal D-alanine-D-alanine;

a D,D-carboxypeptidase capable of cleaving the terminal D-alanine from the substrate to yield a cleaved substrate;

a ligand specific to the substrate or the cleaved substrate; and a binding partner of the ligand specific to the substrate or the cleaved substrate, wherein the binding partner is capable of being bound on a sensing surface.

29. The kit of claim 28 wherein the ligand specific to the substrate or the cleaved substrate is an antibody.

30. The kit of claim 28 wherein the binding partner of the ligand specific to the substrate is substrate, and the binding partner of the ligand specific to the cleaved substrate is cleaved substrate.

* * * * *